(12) United States Patent
Manli

(10) Patent No.: US 8,157,903 B2
(45) Date of Patent: Apr. 17, 2012

(54) GAS-ABSORBING SYSTEM

(75) Inventor: Wu Manli, Beijing (CN)

(73) Assignee: Beijing Aeonmed Co., Ltd., Beijing (CN)

( * ) Notice: Subject to any disclaimer, the term of this patent is extended or adjusted under 35 U.S.C. 154(b) by 315 days.

(21) Appl. No.: 12/348,863

(22) Filed: Jan. 5, 2009

(65) Prior Publication Data

US 2009/0320862 A1    Dec. 31, 2009

(30) Foreign Application Priority Data

Jun. 26, 2008   (CN) .......................... 2008 1 0115692

(51) Int. Cl.
    *B01D 53/02* (2006.01)
(52) U.S. Cl. ............... 96/108; 95/90; 128/910; 137/312
(58) Field of Classification Search ........ 95/90; 96/108; 128/910; 137/312
    See application file for complete search history.

(56) References Cited

U.S. PATENT DOCUMENTS

| | | | | |
|---|---|---|---|---|
| 2,138,153 A * | 11/1938 | Grisdale | ........................ | 422/217 |
| 3,871,842 A * | 3/1975 | Queiser et al. | ................... | 96/131 |
| 3,914,995 A * | 10/1975 | Yoshida | ...................... | 73/114.32 |
| 4,015,959 A * | 4/1977 | Grote | .............................. | 96/136 |
| 4,312,339 A * | 1/1982 | Thompson, Sr. | .......... | 128/205.25 |
| 4,425,143 A * | 1/1984 | Nishizawa et al. | .............. | 95/126 |
| 4,432,777 A * | 2/1984 | Postma | ............................ | 95/151 |
| 4,456,008 A * | 6/1984 | Clawson et al. | .......... | 128/205.19 |
| 4,502,876 A * | 3/1985 | Behnke et al. | ................... | 96/147 |
| 4,527,558 A * | 7/1985 | Hoenig | ...................... | 128/205.24 |
| 4,559,066 A * | 12/1985 | Hunter et al. | ................. | 96/117.5 |
| 4,608,976 A * | 9/1986 | Suchy | ....................... | 128/204.26 |
| 4,676,239 A * | 6/1987 | Humphrey | ............... | 128/205.17 |
| 4,691,700 A * | 9/1987 | Brychta et al. | ........... | 128/200.21 |
| 4,764,346 A * | 8/1988 | Lewis et al. | .................... | 422/120 |
| 4,778,492 A * | 10/1988 | Dawson | .......................... | 95/113 |
| 4,859,405 A * | 8/1989 | Squarer et al. | ................. | 376/299 |
| 5,005,363 A * | 4/1991 | Larin | .............................. | 62/55.5 |
| 5,348,573 A * | 9/1994 | Tomassian et al. | ............. | 96/151 |
| 5,630,409 A * | 5/1997 | Bono et al. | ............... | 128/200.18 |
| 5,851,269 A * | 12/1998 | Strope | ............................. | 96/144 |
| 6,363,931 B1 * | 4/2002 | Dellenbusch | ................ | 128/202.27 |
| 6,736,140 B1 * | 5/2004 | Baczkowski | ............. | 128/206.21 |
| 2006/0076013 A1 * | 4/2006 | Berg | ......................... | 128/203.12 |
| 2006/0090651 A1 * | 5/2006 | Liu et al. | .......................... | 96/121 |
| 2007/0056442 A1 * | 3/2007 | Bres et al. | .......................... | 95/96 |

* cited by examiner

*Primary Examiner* — Robert J Hill, Jr.
*Assistant Examiner* — Christopher P Jones
(74) *Attorney, Agent, or Firm* — Sawyer Law Group, P.C.

(57) ABSTRACT

The present invention provides a gas absorbing system which comprises: an inlet pipe, a gas accommodating section into which gas enters through the inlet pipe, and a negative pressure exhausting pipe which exhausts the gas in the gas accommodating section to external device by using negative pressure wherein the gas accommodating section comprises a first chamber which is provided with air holes in the side wall for discharging the gas in the gas accommodating section or allowing external air entering the gas accommodating section. The gas absorbing system according to the present invention not only can effectively prevent the system internal gas from discharging directly to environment to endanger the health of patients and medical care personnel, but also can reduce the variation of the pressure inside the system when an abnormal incident occurs, so as to prevent it from influencing the safety of the patient to the most extent.

12 Claims, 5 Drawing Sheets

GAS-ABSORBING SYSTEM

CROSS-REFERENCE TO RELATED APPLICATIONS

Under 35 U.S.C. 119, this application claims priority to Chinese patent application No. 200810115692.9 filed Jun. 26, 2008.

FIELD OF THE INVENTION

The present invention relates to a gas-absorbing system, particularly to a gas-absorbing system used for absorbing anesthetic gas in the medical field.

BACKGROUND

When an anesthetic machine is used in an operating room, the gas discharged from the exhaust gas side of the anesthetic machine includes anesthetic exhaust gas. The air environment in the operating room will be contaminated if the anesthetic exhaust gas is directly discharged into the operating room, which may do harm to the health of the medical care personnel and patients in the operating room. Moreover, with the existing anesthetic gas absorbing device, a failure tends to occur frequently due to the improper construction or other reasons, resulting in exceeding variation of the pressure inside the system, which may in turn endanger the safety of the patient. Accordingly, a system and method is required to address the above-identified issues. The present invention addresses such a need.

SUMMARY OF THE INVENTION

The present invention is a system and method in accordance with the present invention which provides a gas absorbing system. The system is especially applicable for absorbing the anesthetic exhaust gas discharged from the anesthetic machine and has an appropriate construction capable of absorbing the anesthetic exhausting gas discharged in various situations of the operation, so as to reduce to the maximum extent the harm to the medical care personnel and patients due to the anesthetic exhaust gas.

To achieve the above objectives, the present invention provides a gas absorbing system which is used with the gas having a larger density than that of air. The absorbing system comprises: an inlet pipe; a gas accommodating section into which the gas enters through the inlet pipe; and a negative pressure exhausting pipe by which the gas within the gas accommodating section is exhausted to an external device, wherein the gas accommodating section comprises a first chamber which is provided with air holes through the side wall thereof to exhaust the gas in the gas accommodating section or allow the external air entering into the gas accommodating section. Preferably, the air holes are disposed in the upper side wall of the first chamber.

Preferably, the gas accommodating section further comprises a second chamber which is housed in the first chamber and communicated with the first chamber through its opened bottom. The inlet pipe passes through the side wall of the second chamber to direct the gas into the second chamber. The negative pressure exhausting pipe is in fluid communication with the top of the second chamber such that the gas in the gas accommodating section is discharged from the negative pressure exhausting pipe via the top. Preferably, the air holes are provided in the lower side wall of the first chamber.

Furthermore, the gas absorbing system further comprises a stop valve interposed between the gas accommodating section and the negative pressure exhausting pipe, for controlling the flow rate of the gas exhausted from the negative pressure exhausting pipe.

Furthermore, the gas absorbing system also comprises a floater which is interposed between the gas accommodating section and the stop valve. The magnitude relationship between the flow rate of the gas entering the inlet pipe and the flow rate of the gas exhausted from the negative pressure exhausting pipe is determined by the up and down floating of the floater so as to facilitate the adjustment of the stop valve and thus control the flow rate of the gas exhausted from the negative pressure exhausting pipe.

Preferably, the floater is accommodated in a floater chamber which is made of transparent material and air-tightly connected to the gas accommodating section.

Preferably, the exit of the inlet pipe faces to the bottom of the first chamber so as to direct the gas from the inlet pipe toward said bottom.

Preferably, the second chamber extends downward to close to the bottom of the first chamber.

Preferably, the opened bottom of the second chamber is spaced from the bottom of the first chamber by 20-30 mm.

The gas absorbing system according to the present invention can reduce the variation of the system internal pressure and effectively prevents the gas in the system from discharging directly into the ambient air, therefore harming the health of the patients and medical care personnel is minimized. The variation of the pressure inside the system can be reduced when an accident occurs, such that the danger imposed on the patient is avoided.

BRIEF DESCRIPTION OF THE DRAWINGS

The above and other aspects, features and other advantages of the present invention will be more understandable through the following detailed description in conjunction with the figures wherein like referential number denotes like element, in which.

DETAILED DESCRIPTION OF THE PREFERRED EMBODIMENTS

The present invention relates to a gas-absorbing system, particularly to a gas-absorbing system used for absorbing anesthetic gas in the medical field. Referring to the figures, the present invention will be described in detail with an anesthetic exhaust gas absorbing system, as an example, used in a medical operation. However, the present invention can be embodied in various forms and should not be construed as being limited to the embodiments set forth herein. On the contrary, the embodiments are provided for making the present disclosure completed and conveying comprehensively the scope of the present invention to those skilled in the art.

Firstly, the construction of the anesthetic exhaust gas absorbing system according to the embodiment of the present invention will be described in conjunction with FIGS. 1, 2 and 5.

Figure 1:
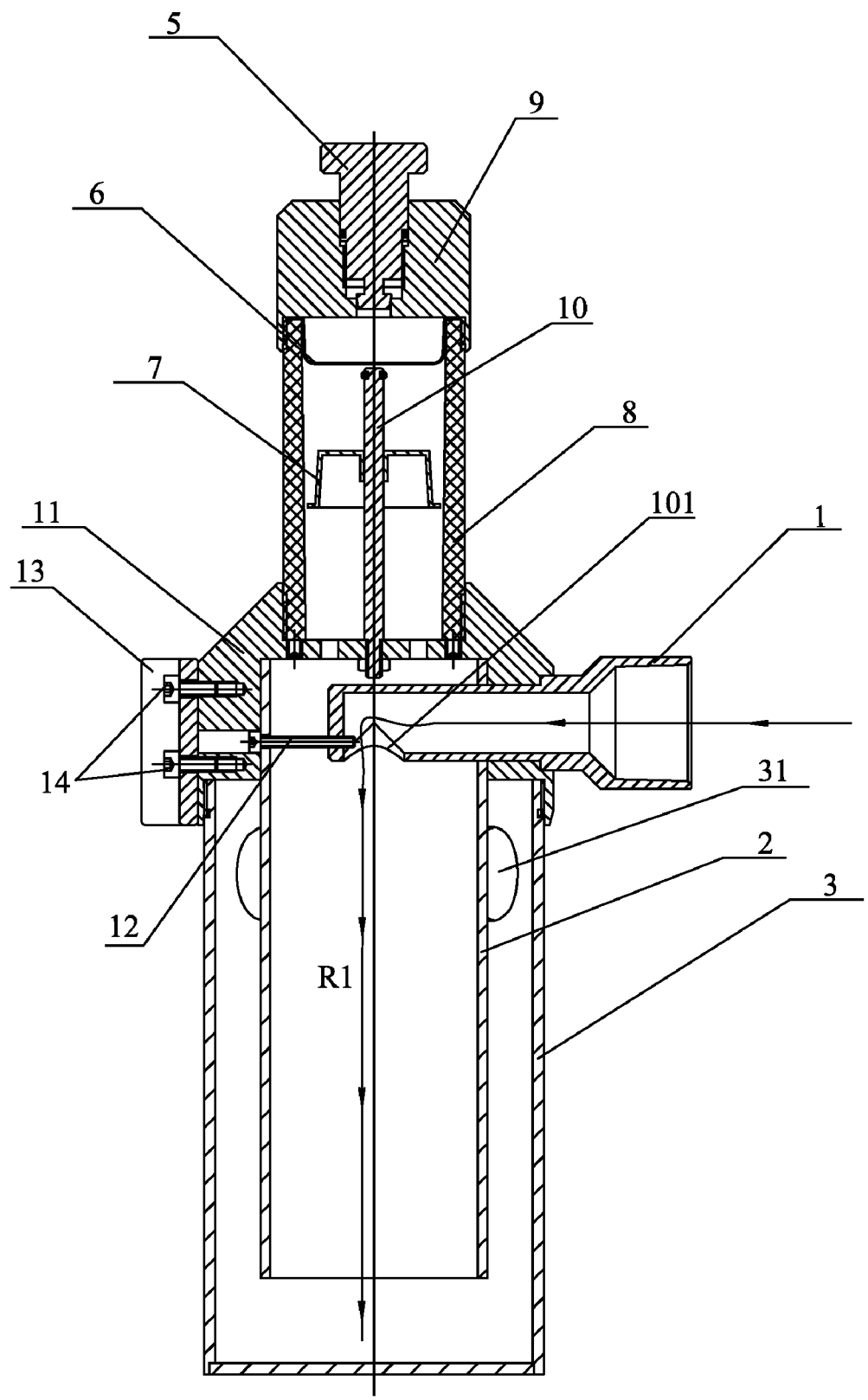
FIG. 1 is a sectional view of the anesthetic exhaust gas absorbing system according to an embodiment of the present invention, wherein the flow path of the anesthetic exhaust gas entering the gas accommodating section from the inlet pipe is shown.
Figure 2:
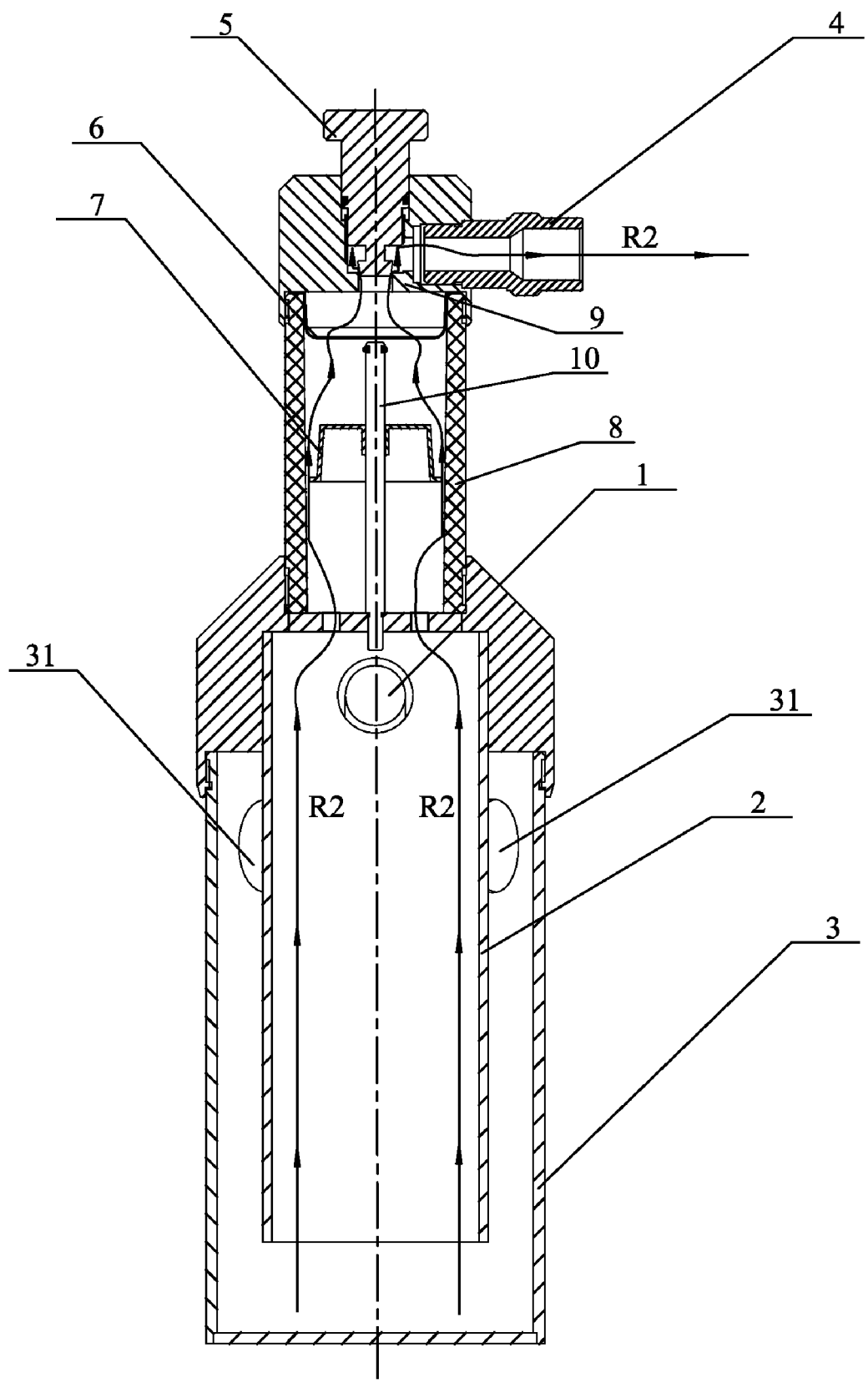
FIG. 2 is another sectional view of the anesthetic exhaust gas absorbing system according to the embodiment of the present invention, wherein the flow path of the anesthetic exhaust gas in the gas accommodating section exhausted to an external device through the negative pressure exhausting pipe under normal conditions is shown.

FIGS. 1 and 2 are sectional views of the anesthetic exhaust gas absorbing system viewed from different directions respectively. FIG. 5 is an exploded view showing schematically the anesthetic exhaust gas absorbing system according to the embodiment of the present invention.

Figure 5:
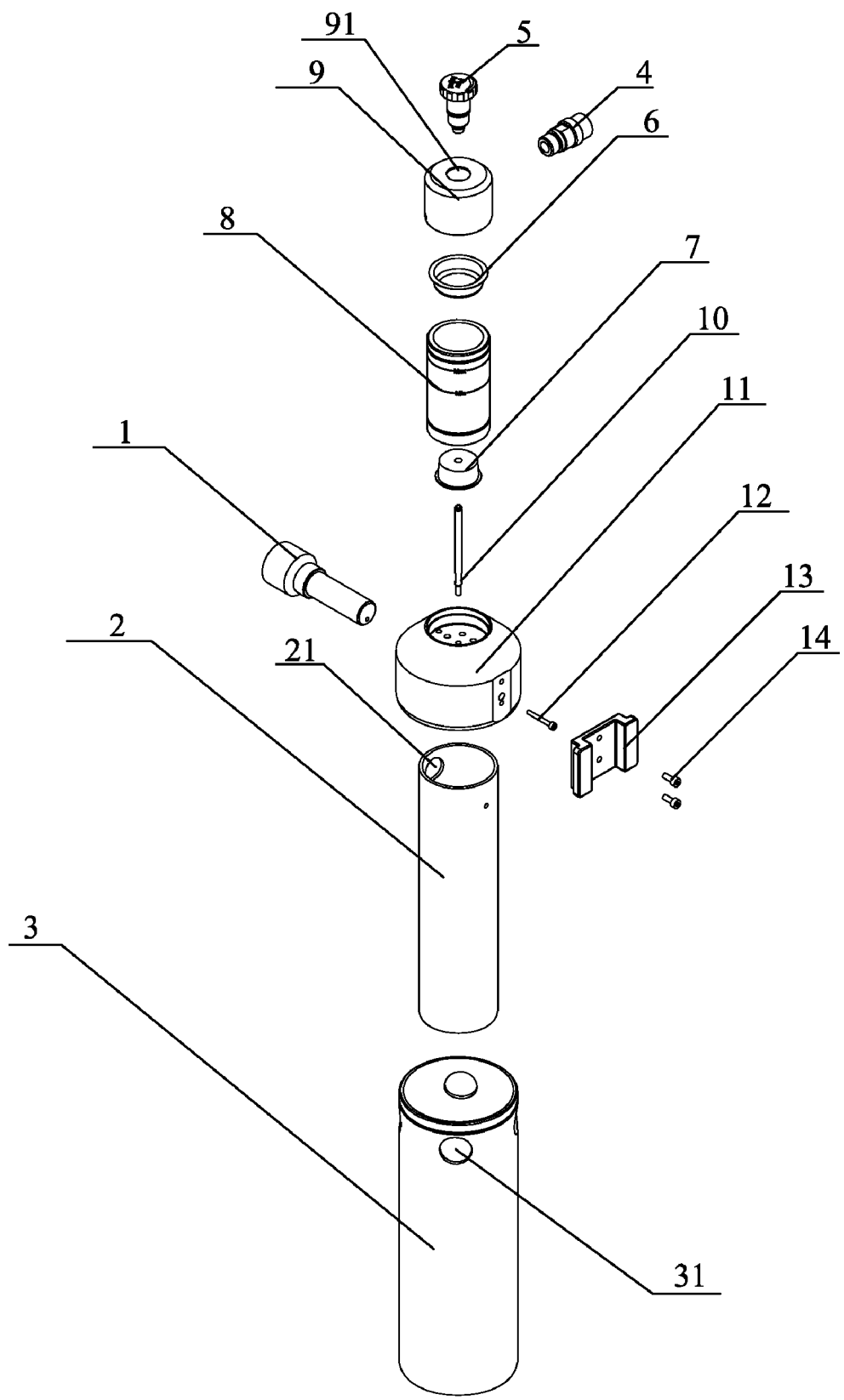
FIG. 5 is an exploded view schematically showing the anesthetic exhausting gas absorbing system according to the embodiment of the present invention.

As shown in FIG. 5, the anesthetic exhaust gas absorbing system according to the embodiment comprises: an inlet 1; a gas accommodating section which is formed by an inner chamber 2 and an outer chamber 3; and a negative pressure exhausting pipe 4. The inlet pipe 1 passes through one side of the inner chamber 2 and is secured to the other side of the inner chamber 2 through a bolt 12. The anesthetic exhaust gas enters the inner chamber 2 through the inlet pipe 1 and flows to the bottom of the inner chamber 2 along the path R1 (as shown in FIG. 1). The negative pressure exhausting pipe 4 is fluid communicated with the top of the inner chamber 2 and exhausts the anesthetic exhaust gas in the gas accommodating section to an external device by using the negative pressure produced by a negative pressure pump (not shown). The outer chamber 3 is provided with air holes 31 at the upper side wall, whose function will be described in detail later.

In this embodiment, the inner chamber 2 is embedded in the outer chamber 3 and communicated with the outer chamber 3 through the opened bottom. The outer chamber 3 is air-tightly joined with a bracket 11. The inlet pipe 1 passes through the through hole 21 a in the side wall of the inner chamber 2 via the bracket 11 and extends into the inner chamber 2. The anesthetic exhaust gas in the gas accommodating section passes through the plural holes in the bracket 11 via the top of the inner chamber 2 and flows into the negative pressure exhausting pipe.

The anesthetic exhaust gas absorbing system according to the embodiment also comprises a floater 7 and a stop valve 5. The floater 7 is movable up and down along the floater bar 10 and accommodated in a floater chamber 8. The floater chamber 8 is made of transparent material such that the operation personnel can view the movement of the floater 7 from outside. The floater chamber 8 is air-tightly connected at one side to the bracket 11 and at the other side to the floater cover 9. The negative pressure exhausting pipe 4 passes sideward through the side wall of the floater cover 9 and extends to the through hole 91. From the above, the stop valve 5 is mounted in the through hole 91 of the floater cover 9 and used for adjusting the flow rate of the anesthetic exhaust gas exhausted from the negative pressure exhausting pipe 4. Preferably, a filter mesh 6 is further provided on the upper portion of the floater chamber 8 so as to filter the anesthetic exhaust gas entering the negative pressure exhausting pipe.

As shown in FIG. 1, the bracket 11 of the anesthetic exhaust gas absorbing system is secured to the base 13 through bolt 14 so as to connect the whole system with external devices such as an anesthetic machine to perform the relative operation.

Alternatively, in an embodiment not shown, the gas accommodating section of the anesthetic exhaust gas absorbing system can merely comprise the outer chamber 3 but not the inner chamber 2. In such a case, preferably, air holes 31 are provided in the lower side wall of the outer chamber 3 to prolong the distance over which the anesthetic exhaust gas flows to the bottom of the outer chamber, preventing the anesthetic exhaust gas from being discharged via the air holes directly after entering the gas accommodating section, which may produce abrupt pressure variation at the inlet pipe.

Hereinafter, the operation of the anesthetic exhaust gas absorbing system according to the embodiment of the present invention will be described in conjunction with FIGS. 1-4.

FIG. 1 is the sectional view of the anesthetic exhaust gas absorbing system according to the embodiment of the present invention wherein the flow path of the anesthetic exhaust gas entering the gas accommodating section from the inlet pipe is shown. As shown in FIG. 1, the anesthetic exhaust gas (whose density is more than that of air) flows downward through the inlet pipe 1 and enters the inner chamber 2 of the gas accommodating section along the path R1. In this embodiment, preferably, the exit 101 of the inlet pipe 1 positioned within the inner chamber 2 is parallel with the axis of the inner chamber 2 and faces toward the bottom thereof, such that the anesthetic exhaust gas is effectively directed to the bottom of the inner chamber 2 from the inlet pipe 1. The anesthetic exhaust gas is prevented from being directly discharged from the negative pressure exhausting pipe 4, the pressure variation at the inlet pipe 1 is effectively reduced, and pressure variation is avoided to establish negative pressure at the inlet pipe 1 to endanger the patient. Moreover, since the opened bottom of the inner chamber 2 extends to close to the bottom of the outer chamber 3 (preferably, the bottom of the inner chamber 2 is spaced from the bottom of the outer chamber 3 by 20-30 mm), the gas accommodating section has compact construction. Therefore, the anesthetic exhaust gas is more easily exhausted from the negative pressure exhausting pipe 4 when flowing upward, such that the amount of anesthetic exhaust gas discharged into atmosphere through the air holes 31 in the upper side of the outer chamber is effectively reduced (the air holes 31 is preferably provided in the upper side wall of the outer chamber 3 so as to reduce the leak of anesthetic exhaust gas).

FIG. 2 is another sectional view of the anesthetic exhaust gas absorbing system according to the embodiment of the present invention, showing the flow path of the anesthetic exhaust gas in the gas accommodating section discharged to the external device through the negative pressure exhausting pipe 4 under normal condition. Under the normal operating condition of the anesthetic exhaust gas absorbing system, due to the effect of the negative pressure pump positioned at the negative pressure exhausting pipe 4, the pressure at the negative pressure exhausting pipe 4 is lower than the pressure inside the absorbing system. In addition, the anesthetic exhaust gas flows along the direction of path R2 and is exhausted from the negative exhausting pipe 4 to the external device such as a disposing system after being adjusted at the flow rate by the stop valve 5 (the adjustment can be performed according to the up and down floating of the floater 7).

Figure 3:
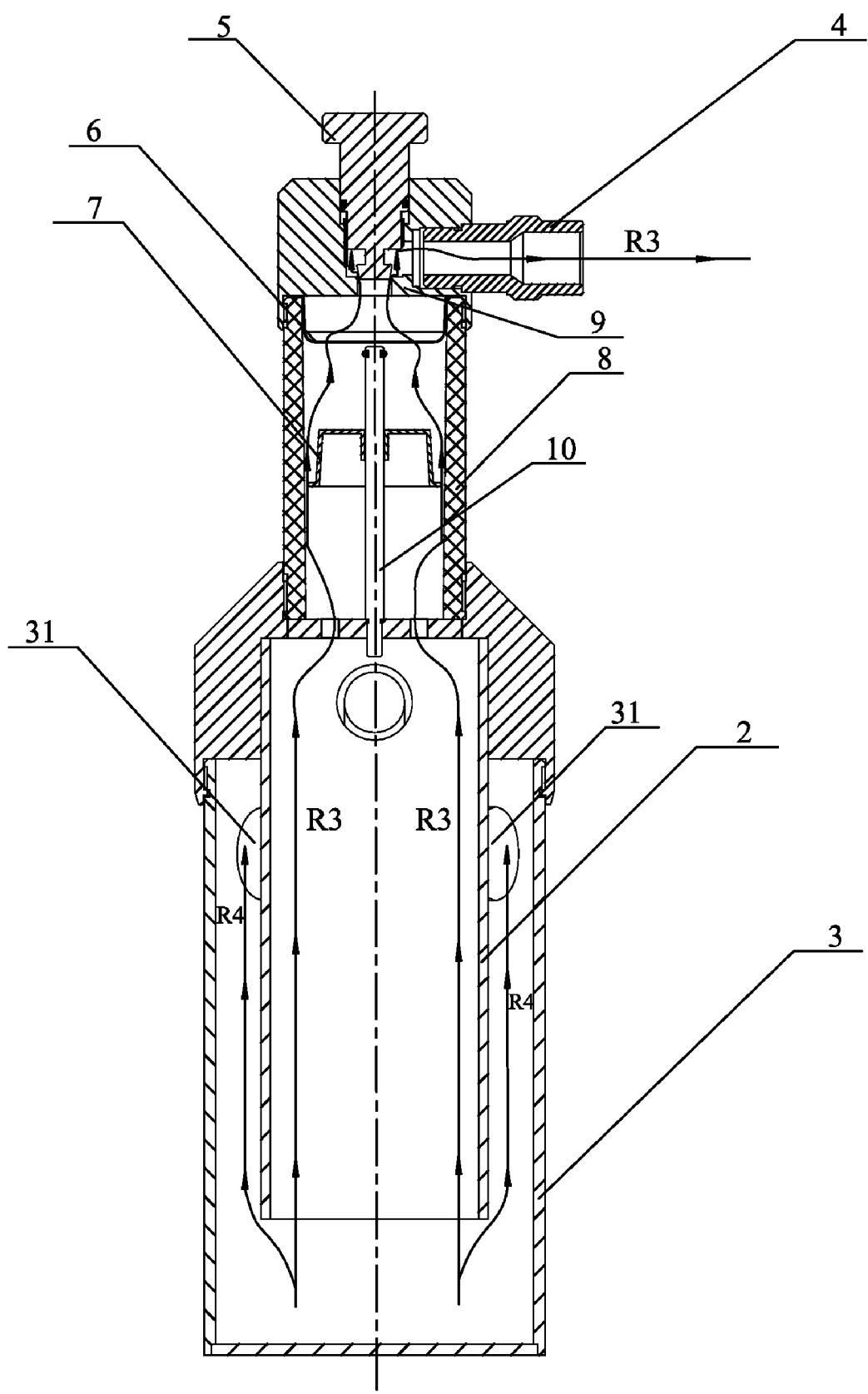
FIG. 3 is another sectional view of the anesthetic exhaust gas absorbing system according to the present invention, wherein it is shown the flow path of the anesthetic exhaust gas in the gas accommodating section when the input flow rate of the exhaust gas from the inlet pipe is greater than the output flow rate of the gas exhausted from the negative pressure exhaust pipe (which is an abnormal condition)

FIG. 3 is another sectional view of the anesthetic exhaust gas absorbing system according to the embodiment of the present invention, showing the flow path of the anesthetic exhaust gas in the gas accommodating section when the input flow rate of the exhaust gas from the inlet pipe is instantly greater than the output flow rate of the exhaust gas discharged from the negative pressure exhausting pipe due to an abnormal accident. As shown in FIG. 3, when the input flow rate of the exhaust gas from the inlet pipe 1 is greater than the output flow rate of the exhaust gas exhausted from the negative pressure exhausting pipe 4 due to certain failures (e.g. the output flow rate of exhaust gas is reduced due to the abnormity of the negative pressure exhausting pipe 4, or the input flow rate of exhaust gas of the inlet pipe 1 is too high for short time), part of the anesthetic exhaust gas passes through the floater chamber 8 along the path R3 and is filtered by the filter mesh 6 so as to exhausted to the external device from the negative pressure exhausting pipe 4. The remaining anesthetic exhaust gas, which is unable to be exhausted in time, can be discharged to the outdoor through the air holes 31 in the outer chamber 3 along the path R4, such that the inlet pipe 1 is prevented from producing pressure increment to endanger the safety of the patient. In this way, it saves more time for the operation personnel to discover and solve the problem.

Figure 4:
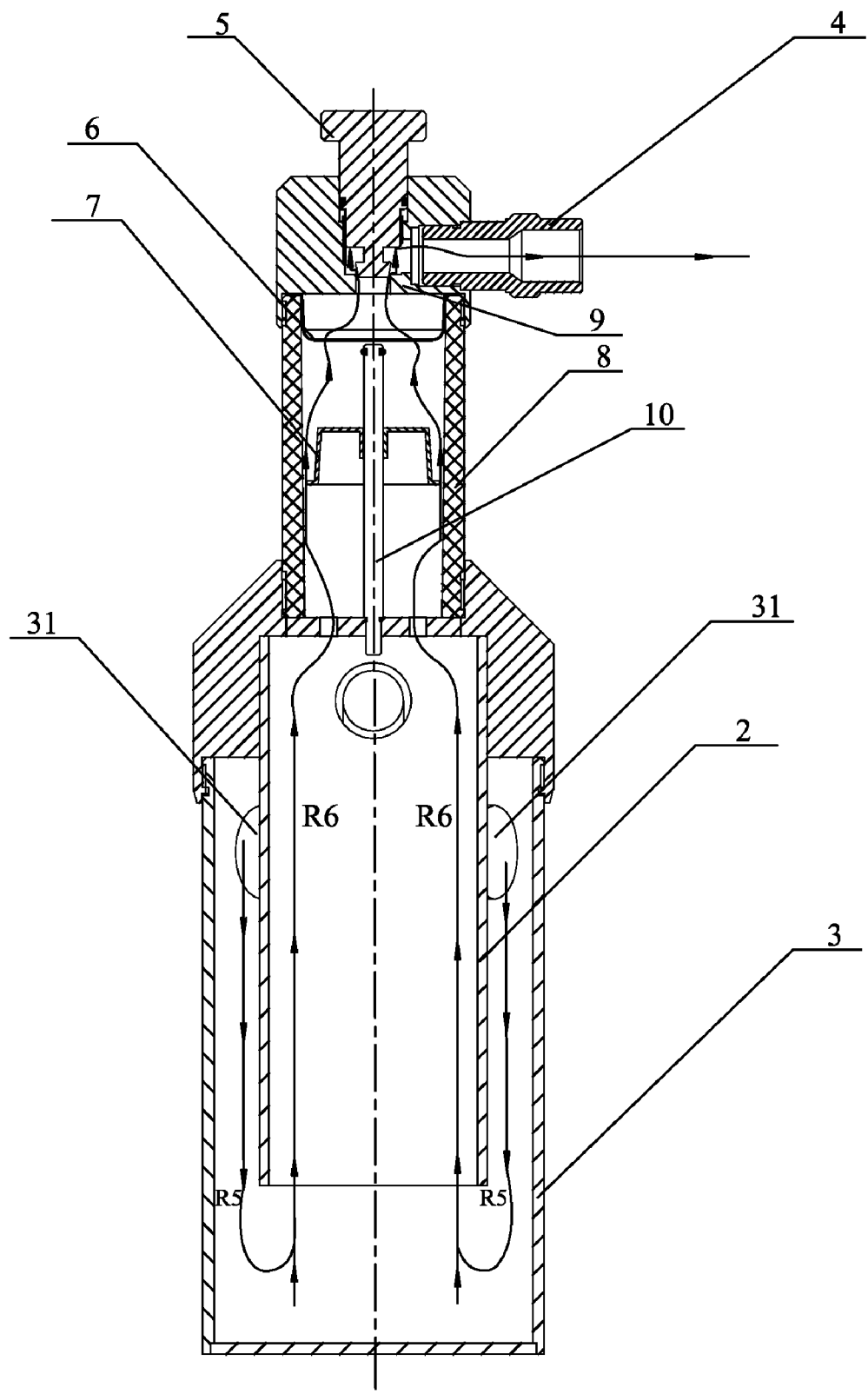
FIG. 4 is another sectional view of the anesthetic exhaust gas absorbing system according to the embodiment of the present invention, wherein it is shown the flow path of the anesthetic exhaust gas in the gas accommodating section when the output flow rate of the exhaust gas exhausted from the negative pressure exhaust pipe is greater than the input flow rate of the exhaust gas from the inlet pipe (which is another abnormal condition)

FIG. 4 is another sectional view of the anesthetic exhaust gas absorbing system according to the embodiment of the present invention, showing the flow path of the anesthetic exhaust gas in the gas accommodating section when the output flow rate of the exhaust gas exhausted from the negative pressure exhausting pipe is instantly greater than the input flow rate of the exhaust gas from the inlet pipe due to another abnormal incident. As shown in FIG. 4, when the output flow rate of the exhaust gas exhausted from the negative pressure exhausting pipe 4 is greater than the input flow rate of the exhaust gas from the inlet pipe, external air is supplied into the gas accommodating section through the air holes 31 in the outer chamber 3 along the path R5. The external air enters the inner chamber 2 and proceeds along with the anesthetic exhaust gas, passes through the floater chamber 8 along the path R6 and is filtered by the filter mesh 6 to be exhausted to the disposing system from the negative pressure exhausting pipe 4. The inlet pipe is prevented from producing negative pressure to endanger the safety of the patient. Also more time is saved for the operation personnel to discover and solve the problem.

In this embodiment, the stop valve 5 adjusts the magnitude of the flow rate of the anesthetic exhaust gas entering the negative pressure exhausting pipe 4, so as to reduce the load and noise of the negative pressure pump at the negative pressure exhausting pipe 4. Meanwhile, during the adjustment of the stop valve 5, the operator can view the up and down movement of the floater 7 along the floater bar 10 through the transparent floater chamber 8, so as to effectively adjust the flow rate, avoiding the variation of the pressure inside the system from endangering the safety of the patient.

The above is only the description of the preferable embodiment of the present invention and is not intended to limit the present invention. As for those skilled in the art, without departing from the spirit and principle of the present invention, various changes and variations can be made to the present invention. All such changes, substitutions and improvements should be contained in the scope of the present invention.

What is claimed:

1. A gas absorbing system comprising:

an inlet pipe;

a gas accommodating section into which gas enters through the inlet pipe; and a negative pressure exhausting pipe which exhausts the gas in the accommodating section to an external device by using negative pressure, characterized in that, the gas accommodating section comprises a first chamber which is provided with air holes in its side wall, wherein the air holes are in direct air communication with the exterior of said gas absorbing system without passing through the negative pressure exhausting pipe such that gas in the gas accommodating section can be exhausted through the air holes to the exterior or that external air in the exterior can enter through the air holes into the gas accommodating section.

2. The gas absorbing system according to claim 1, wherein the air holes are disposed in the lower side wall of the first chamber.

3. The gas absorbing system according to claim 1, wherein the gas accommodating section further comprises a second chamber which is housed in the first chamber and communicated with the first chamber through its opened bottom, the inlet pipe passes through the side wall of the second chamber to direct the gas to into the second chamber, and the negative pressure exhausting pipe is communicated with the top of the second chamber such that the gas in the gas accommodating section is discharged from the negative pressure exhausting pipe via the top.

4. The gas absorbing system according to claim 3, wherein the air holes are disposed in the upper side wall of the first chamber.

5. The gas absorbing system according to claim 3, wherein the gas absorbing system further comprises a stop valve which is interposed between the gas accommodating section and the negative pressure exhausting pipe for controlling the flow rate of the gas exhausted from the negative pressure exhausting pipe.

6. The gas absorbing system according to claim 3, wherein the exit of the inlet pipe is facing to the bottom of the first chamber to direct the gas from the inlet pipe toward the bottom.

7. The gas absorbing system according to claim 3, wherein the second chamber extends downward to close to the bottom of the first chamber.

8. The gas absorbing system according to claim 7, wherein the opened bottom of the second chamber is spaced from the bottom of the first chamber by 20-30 mm.

9. The gas absorbing system according to claim 1, wherein the gas absorbing system further comprises a stop valve which is interposed between the gas accommodating section and the negative pressure exhausting pipe for controlling the flow rate of the gas exhausted from the negative pressure exhausting pipe.

10. The gas absorbing system according to claim 9, wherein the gas absorbing system further comprises a floater which in interposed between the gas accommodating section and the stop valve and whose up and down floating is used for adjusting the magnitude relationship between the flow rate of the gas entering the inlet pipe and that of the gas exhausted from the negative pressure exhausting pipe, so as to adjust the stop valve and thus control the flow rate of the gas exhausted from the negative pressure exhausting pipe.

11. The gas absorbing system according to claim 10, wherein the floater is accommodated in a floater chamber made of transparent material and air-tightly connected to the gas accommodating section.

12. The gas absorbing system according to claim 1, wherein the exit of the inlet pipe is facing to the bottom of the first chamber to direct the gas from the inlet pipe toward the bottom.

* * * * *